(12) United States Patent
Otto

(10) Patent No.: US 10,781,960 B2
(45) Date of Patent: Sep. 22, 2020

(54) THROTTLE AND INFUSION PUMP WITH THROTTLE

(71) Applicant: tricumed Medizintechnik GmbH, Kiel (DE)

(72) Inventor: Karl-Heinz Otto, Kiel (DE)

(73) Assignee: tricumed Medizintechnik GmbH, Kiel (DE)

(*) Notice: Subject to any disclaimer, the term of this patent is extended or adjusted under 35 U.S.C. 154(b) by 0 days.

(21) Appl. No.: 16/137,926

(22) Filed: Sep. 21, 2018

(65) Prior Publication Data
US 2020/0096148 A1    Mar. 26, 2020

(51) Int. Cl.
*F16L 55/027*    (2006.01)

(52) U.S. Cl.
CPC ............................. *F16L 55/02772* (2013.01)

(58) Field of Classification Search
CPC ......... F16L 55/02772; A61M 5/14228; A61M 2005/14506
USPC ...................................... 138/42, 39; 604/131
See application file for complete search history.

(56) References Cited

U.S. PATENT DOCUMENTS

| | | | | |
|---|---|---|---|---|
| 4,537,680 A | * | 8/1985 | Barth | A61M 5/165 210/316 |
| 5,143,630 A | * | 9/1992 | Rolchigo | B01D 29/055 210/780 |
| 5,908,414 A | * | 6/1999 | Otto | A61M 5/14276 604/141 |
| 8,808,223 B2 | * | 8/2014 | Barr | A61M 5/16881 604/9 |
| 2007/0043335 A1 | * | 2/2007 | Olsen | A61M 5/14276 604/890.1 |
| 2008/0041481 A1 | * | 2/2008 | Mudd | G01F 1/40 138/42 |
| 2009/0326517 A1 | * | 12/2009 | Bork | A61M 5/14276 604/891.1 |
| 2010/0168672 A1 | * | 7/2010 | Carr | A61M 5/14248 604/153 |

* cited by examiner

*Primary Examiner* — Patrick F Brinson
(74) *Attorney, Agent, or Firm* — Diederiks & Whitelaw, PLC

(57) ABSTRACT

Throttle with a throttle path formed from two plane-parallel plates connected with one another, wherein the throttle path include a trough formed in at least one of the two plates and sealed by the other plate, which exhibits on one end an inlet which communicates with the throttle path and on the other end an outlet which communicates with the throttle path, characterized in that both plates are made of glass.

14 Claims, 1 Drawing Sheet

FIG. 1A
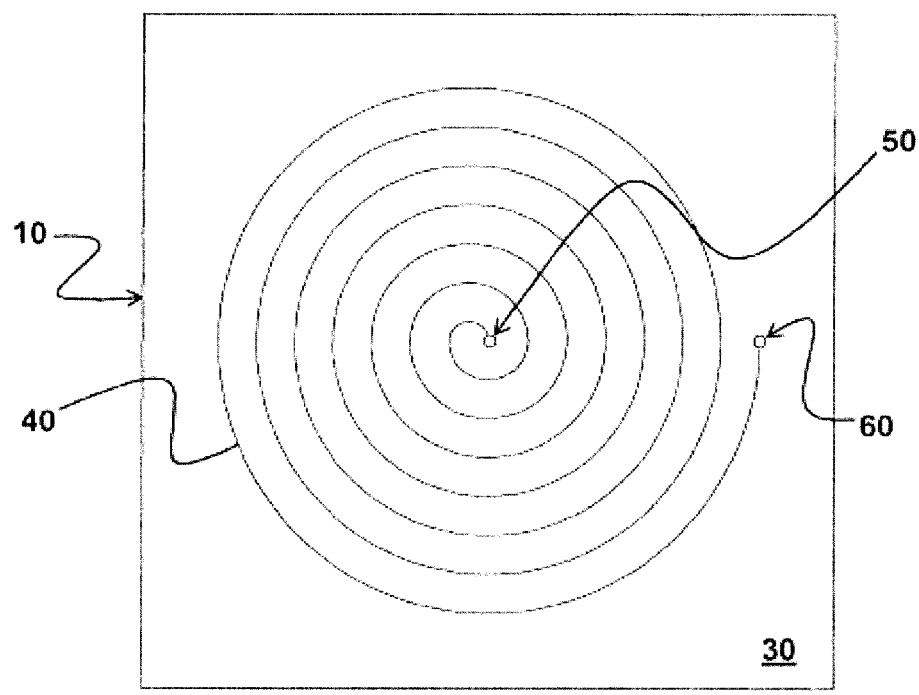
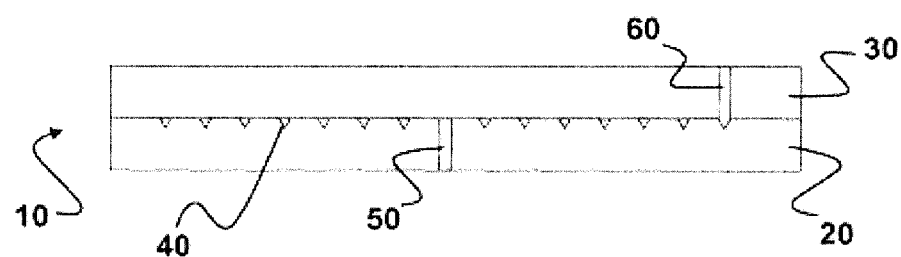
FIG. 1B

THROTTLE AND INFUSION PUMP WITH THROTTLE

FIELD OF THE INVENTION

The invention pertains to a throttle for an implantable infusion pump as well as an infusion pump with a throttle of this type.

BACKGROUND OF THE INVENTION

Implantable infusion pumps are well-known for providing constant intrathecal long-term medication. Implantable infusion pumps are used especially in pain management and spasticity treatment and make it possible for patients to live a largely normal and symptom-free life. Because of the low, consistent medication dosage of approximately 1/100 of the corresponding oral dosage, side effects of the respective medication administered are drastically reduced.

In order to facilitate a continuous, consistent medication dosage, a throttle with a predetermined throttle path is provided between a medication reservoir and a pump outlet which determines the flow rate and, together with the volume of the reservoir, the filling interval of the infusion pump.

Originally, a linear glass capillary provided with an outer coating and having a predetermined diameter was used. The capillary was wound into a roll, also called a "coil". The disadvantage of this type of throttle is that the diameter of the capillary is subject to considerable variations along its length, i.e. along the throttle path. Thus, the labor and material expenditure in producing implantable infusion pumps is increased due to the choice of suitable capillary sections. Furthermore, a certain degree of skill and experience is required for the production of such throttles, and even then, a relatively high degree of waste of capillary material—on the order of 10-15%—must be taken into account.

So-called "chip capillaries" address this problem. The chip capillaries provide a throttle with a throttle path formed from two plane-parallel plates connected with one another, whereby the throttle path includes a trough formed in at least one of the two plates and sealed by the other plate. On one end, an inlet communicates with the throttle path and on the other end, an outlet communicates with the throttle path. In the case of the "chip capillary", the plate exhibiting the troughs is made from silicon and the capillary covering the troughs is made from glass.

The "chip capillary" certainly has advantages in terms of constant production with low tolerances under clean room conditions and the miniaturization of the throttle and therefore the pump. However, a miniaturized throttle designed as a "chip capillary" also exhibits disadvantages. In particular, the use of silicon plates is problematic in terms of their chemical resistance within a neutral pH range, such that medications with a basic pH can destroy the fine structures in the silicon plate which make up the throttle path and thus lead to a short circuit between the medication reservoir and the outlet.

Therefore, the goal of the invention is to create a throttle for an implantable infusion pump which is ideal for medications, regardless of their pH value, especially for medications with basic pH values. A further goal of the invention is to create an implantable infusion pump with which medications can be infused regardless of their pH value, especially medications with basic pH values, without risking damage or destruction of the infusion pump or its throttle.

SUMMARY OF THE INVENTION

A first basic principle of the invention is to create a throttle for an implantable pump whose components are formed entirely of glass. This measure can prevent medications with a basic pH value from attacking the structure of the throttle path, as glass is resistant to basic pH values.

Another basic principle of the invention is to form the throttle path in the shape of an Archimedean spiral. Thus, a long throttle path can be realized within a small space, wherein due to the laminar flow conditions in the Archimedean spiral, the accumulation of particles within the spiral can be simultaneously prevented.

Thus the invention provides a throttle with a throttle path formed from two plane-parallel plates connected with one another, whereby the throttle path includes a trough formed in at least one of the two plates and sealed by the other plate. The throttle exhibits on one end, an inlet which communicates with the throttle path and on the other end, an outlet which communicates with the throttle path, and wherein both plates are made of glass.

According to a first preferred embodiment, the throttle path is formed as an Archimedean spiral. In comparison to the typical designs known from the prior art with production-related geometry of the throttle path in the form of spirally-arranged lengths, the preferred design of the Archimedean spiral prevents the deposition of particles present in the medication.

According to a second preferred embodiment, the trough is formed by etching. Preferably, the trough is formed with a laser.

According to a further preferred embodiment, the inlet and/or the outlet extend substantially perpendicular to the throttle path. In particular, the inlet and/or outlet extend through one plate and/or the other plate. The inlet and/or the outlet are especially formed as drilled holes through the respective plate. Most preferably, the inlet is located in one plate and the outlet is located in the other plate.

Furthermore, it is preferable that the inlet is located at the center of the Archimedean spiral and the outlet is located at the end of the Archimedean spiral.

Finally, an infusion pump with a throttle is constructed as previously described. Thus the infusion pump exhibits a medication reservoir and a medication outlet which communicates with the medication reservoir, wherein the throttle is integrated into the medication outlet—as is known. By the use of a throttle in which both plates are made of glass, it is possible to apply medications with basic pH values without deviations in flow rate.

BRIEF DESCRIPTION OF THE DRAWINGS

FIG. 1A hereby shows a top view of the particularly preferred form of the throttle, and FIG. 1B shows a cross-section through the center of the throttle.

DETAILED DESCRIPTION OF THE PREFERRED EMBODIMENTS

The invention is described in greater detail with the assistance of a particularly favored embodiment of a throttle designed in accordance with the invention and depicted in FIGS. 1A and 1B. Preferably throttle 10 exhibits two plane-parallel plates 20, 30 connected to one another, which form a throttle path 40. In the example shown, it can be seen in the top view that the throttle path 40 is formed in the shape of an Archimedean spiral. The inlet 50 of the throttle path 40 is located in the center of the Archimedean spiral and the outlet 60 of the throttle path 40 is located at the outer end of the Archimedean spiral, wherein—as is shown in FIG. 1B—the inlet 50 is located in one plate 20 and the outlet 60 is located in the other plate 30.

The throttle path 40 itself is formed by the trough provided in one plate 20, which is sealed by the other plate 30. Only the inlet 50 and the outlet 60 communicate with the trough which constitutes the throttle path 40, wherein the two plates 20, 30 made of glass are also bonded to one another with a fluid-tight seal. In particular, the two plates 20, 30 consist of the same glass material. The exit of a medication introduced into the throttle 10 is therefore only possible through the outlet 60.

It is preferred that the trough which constitutes the throttle path is formed by etching or by a laser. The exclusive use of glass as plate material makes it possible to channel medications of any pH value, without the structure of the throttle 10, in particular the throttle path 40, being damaged. The construction of the throttle path 40 as an Archimedean spiral thereby also prevents an accumulation of particles within the throttle path, so that a significant miniaturization of the throttle as such is possible.

In a known manner, a filter (not depicted) located inside the infusion pump and upstream of the throttle 10 ensures that the inlet 50 of the throttle 10 does not become blocked by particles and thus the pump function is maintained.

The invention claimed is:

1. A throttle comprising:
   two parallel plates and;
   a throttle path formed from the two parallel plates being connected with one another, wherein the throttle path is formed as an Archimedean spiral and includes a trough formed in at least one of the two plates and sealed by the other plate, an inlet at one end of the path communicates with the trough and an outlet at the other end of the path communicates with the trough, wherein both plates are made of glass, the inlet is located at the center of the Archimedean spiral and the outlet is located at the outer end of the Archimedean spiral.

2. The throttle according to claim 1, wherein the trough is formed by etching.

3. The throttle according to claim 1, wherein the trough is formed with a laser.

4. The throttle according to claim 1, wherein the inlet and/or outlet are substantially perpendicular to the throttle path.

5. The throttle according to claim 4, wherein the inlet and/or outlet extends through one plate and/or the other plate.

6. The throttle according to claim 1, wherein the inlet is located in one plate and the outlet is located in the other plate.

7. An infusion pump comprising:
   a throttle including
   two parallel plates and;
   a throttle path formed from the two parallel plates being connected with one another, wherein the throttle path is formed as an Archimedean spiral and includes a trough formed in at least one of the two plates and sealed by the other plate, an inlet at one end of the path communicates with the trough and an outlet at the other end of the path communicates with the trough, wherein both plates are made of glass, the inlet is located at the center of the Archimedean spiral and the outlet is located at the outer end of the Archimedean spiral.

8. The infusion pump according to claim 7, wherein the trough is formed by etching.

9. The infusion pump according to claim 7, wherein the trough is formed with a laser.

10. The infusion pump according to claim 7, wherein the inlet and/or outlet are substantially perpendicular to the throttle path.

11. The infusion pump according to claim 7, wherein the inlet and/or outlet extends through one plate and/or the other plate.

12. The infusion pump according to claim 7, wherein the inlet is located in one plate and the outlet is located in the other plate.

13. The throttle according to claim 1, wherein the throttle path is configured to cause laminar flow conditions in the Archimedean spiral.

14. The infusion pump according to claim 7, wherein the throttle path is configured to cause laminar flow conditions in the Archimedean spiral.

* * * * *